(12) United States Patent
Schena

(10) Patent No.: US 9,078,686 B2
(45) Date of Patent: Jul. 14, 2015

(54) ROBOTIC SURGICAL SYSTEM WITH PATIENT SUPPORT

(71) Applicant: Bruce Schena, Menlo Park, CA (US)

(72) Inventor: Bruce Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 134 days.

(21) Appl. No.: 13/784,650

(22) Filed: Mar. 4, 2013

(65) Prior Publication Data

US 2013/0178870 A1 Jul. 11, 2013

Related U.S. Application Data

(63) Continuation of application No. 11/963,429, filed on Dec. 21, 2007, now Pat. No. 8,400,094.

(51) Int. Cl.
| | |
|---|---|
| *A61B 19/12* | (2006.01) |
| *A61B 19/00* | (2006.01) |
| *A61G 13/04* | (2006.01) |
| *A61B 17/00* | (2006.01) |

(52) U.S. Cl.
CPC ............ *A61B 19/2203* (2013.01); *A61G 13/04* (2013.01); *A61B 2017/00991* (2013.01)

(58) Field of Classification Search
CPC ............. A61B 1/012; A61B 5/06; B25J 3/00; B25J 9/00; B25J 9/02; B25J 9/06; B25J 9/08; B25J 9/10; B25J 9/16; G01B 7/00; G05B 19/12; G06F 3/02
USPC ............. 318/568.11, 568.12, 568.16, 568.19, 318/568.21, 568.25; 600/117; 601/1
See application file for complete search history.

(56) References Cited

U.S. PATENT DOCUMENTS

| | | | |
|---|---|---|---|
| 4,840,363 | A | 6/1989 | McConnell |
| 5,184,601 | A | 2/1993 | Putman |
| 5,369,825 | A | 12/1994 | Reesby |
| 5,445,166 | A | 8/1995 | Taylor |
| 5,597,146 | A | 1/1997 | Pulman |
| 5,696,837 | A | 12/1997 | Green |
| 5,800,423 | A | 9/1998 | Jensen |
| 5,824,007 | A | 10/1998 | Faraz et al. |
| 5,855,583 | A | 1/1999 | Wang et al. |
| 6,441,577 | B2 | 8/2002 | Blumenkranz et al. |
| 6,739,006 | B2 | 5/2004 | Borders et al. |
| 6,837,883 | B2 | 1/2005 | Moll et al. |
| 6,843,182 | B2 | 1/2005 | Torcheboeuf |
| 6,933,695 | B2 | 8/2005 | Blumenkranz |
| 7,083,571 | B2 | 8/2006 | Wang et al. |
| 7,299,512 | B2 | 11/2007 | Cavalier et al. |
| 8,400,094 | B2 | 3/2013 | Schena |

OTHER PUBLICATIONS

Vertut, Jean Philippe Coiffet, Teleoperation and Robotics: Evolution and Development, English translation Prentice-Hall, Inc., Inglewood Cliffs, NJ, USA, 1986.

*Primary Examiner* — Melanie Hand

(57) ABSTRACT

A robotic surgery system for supporting a patient and a robotic surgical manipulator. The robotic surgery system includes a base, a pillar coupled to the base at a first end and extending vertically upwardly to an opposing second end, and an attachment structure coupled to the second end of the pillar. A patient table is coupled to the attachment structure. A robot support arm has a first end coupled to the attachment structure. The robot support arm extends vertically upwardly from the first end to a second end. The robot support arm may further extend horizontally over the patient table to support a robotic surgical manipulator that will extend generally downward from the robot support arm toward a patient supported by the patient table to place an end effector of the robotic surgical manipulator adjacent a desired surgical site on the patient.

19 Claims, 4 Drawing Sheets

ROBOTIC SURGICAL SYSTEM WITH PATIENT SUPPORT

CROSS REFERENCE TO RELATED APPLICATIONS

This application is a continuation of application Ser. No. 11/963,429, filed Dec. 21, 2007, now U.S. Pat. No. 8,400,094, which is hereby incorporated by reference in its entirety.

BACKGROUND

1. Field

Embodiments of the invention generally relate to surgical devices, systems, and methods, especially for minimally invasive surgery, and more particularly provides structures and techniques for supporting a surgical patient and a robotic surgery system at a desired surgical site.

2. Background

The present invention describes techniques for supporting a patient and robotic surgical manipulators of a robotic surgery system within an operating theater, and methods of improving the stability of the patient-robot system.

Minimally invasive medical techniques are aimed at reducing the extraneous physiologic impact and damage to tissue in carrying out a diagnostic or surgical procedure, thereby reducing patient recovery time, discomfort, and deleterious side effects. The average length of a hospital stay for a standard surgery is significantly longer than the average length for the equivalent surgery performed in a minimally invasive surgical manner. Patient recovery times, patient discomfort, surgical side effects, and time away from work are also reduced with minimally invasive surgery.

In traditional minimally invasive surgery, such as endoscopy, surgical instruments are introduced to an internal surgical site, often through trocar sleeves or cannulas. A body cavity, such as a patient's abdomen, may be insufflated with gas to provide improved access to a surgical site, and cannula or trocar sleeves are passed through small (approximately ½ inch) incisions to provide entry ports for endoscopic surgical instruments. The surgical instruments or tools used in traditional endoscopy may have elongate handles extending out from the cannula, to permit the surgeon to perform surgical procedures by manipulating the tools from outside the body. The portion of the tool inserted into the body may include an end effector, by which tissue is manipulated. Typically minimally invasive procedures are performed under the direction of a surgical imaging system, such as by introducing an endoscope to the surgical site for viewing the surgical field. Typically the endoscope is coupled to a digital camera, to permit remote display, the surgeon then activating the surgical instruments while viewing the surgical site on a video monitor. Similar endoscopic techniques are employed in, e.g., laparoscopy; arthroscopy, retroperitoneoscopy, pelviscopy, nephroscopy, cystoscopy, cisternoscopy, sinoscopy, hysteroscopy, urethroscopy, and the like.

Minimally invasive surgical systems have been and continue to be developed to increase a surgeon's dexterity by means of robotic telesurgical systems, so that the surgeon performs the surgical procedures on the patient by manipulating master control devices to control the motion of servomechanically operated instruments. In contrast to the elongate handles of traditional endoscopic tools, in robotically assisted minimally invasive surgery, or telesurgery, a servomechanism is used to actuate the surgical end effectors of the instruments. This allows the surgeon to operate in a comfortable position without looking one direction (towards the monitor) while manipulating handles of surgical instruments that are oriented in another direction (for example, into the patient's abdomen). Telesurgical or robotically operated instruments also may greatly increase the range of motion and degrees of freedom achievable for end effectors at the internal surgical site.

As more fully described in U.S. Pat. No. 5,696,837, the full disclosure of which is incorporated herein by reference, a computer processor of the servomechanism can be used to maintain the alignment between hand input devices of the controller with the image of the surgical end effectors displayed on the monitor using coordinate system transformations. This allows the surgeon to operate in a natural position using anthropomorphic hand input devices and motions aligned with the image display, despite the fact that the actual surgical instruments are inserted via otherwise awkward arbitrary access positions. The endoscope may optionally provide the surgeon with a stereoscopic image to increase the surgeon's ability to sense three-dimensional information regarding the tissue and procedure. Typically the image captured by the endoscope is digitized by a camera, such as a CCD device, and processed for display to the surgeon and surgical assistants.

In robotically assisted surgery or telesurgery, a surgeon typically operates at least one master controller to control the motion of at least one surgical instrument at the surgical site. The controller will typically include one or more hand input devices or masters, by which the surgeon inputs control movements. The master controllers and surgeon's view display of the endoscope image may be separated from the patient by a significant distance, and need not be immediately adjacent the operating table. The master controller mountings and endoscope display may be integrated as a control console, referred to herein as the "surgeon's console" portion of the telesurgical system, which may be connected by signal and power cables to the servomechanisms, endoscope cameras, processors and other surgical instrumentation. The console is typically located at least far enough from the operating table to permit unobstructed work space for surgical assistants.

Each telesurgical master controller is typically coupled (e.g., via a dedicated computer processor system and connector cables) to a servo-mechanism operating a surgical instrument. The servo mechanism articulates and operates the surgical instrument, tool or end effector to carry out the surgical procedure. A plurality of master controllers may operate a plurality of instruments or end effectors (e.g., tissue graspers, needle drivers, cautery probes, and the like) based on the surgeon's inputs. These tools perform functions for the surgeon, for example, holding or driving a needle, grasping a blood vessel, or dissecting, cauterizing, or coagulating tissue. Similarly, surgeon's master inputs may control the movement and operation of an endoscope-camera driver servomechanism, permitting the surgeon to adjust the view field and optical parameters of the endoscope as the surgery proceeds. In a typical telesurgical system, the surgeon may operate at least two surgical instruments simultaneously, (e.g., corresponding to right and left hand inputs) and operate an endoscope/camera driver by additional control inputs. Note that optionally the servo-manipulators may support and operate a wide variety of surgical tools, fluid delivery or suction devices, electrical or laser instruments, diagnostic instruments, or alternative imaging modalities (such as ultrasound, fluoroscopy, and the like).

U.S. Pat. Nos. 5,184,601; 5,445,166; 5,696,837; 5,800,423; and 5,855,583 describe various devices and linkage arrangements for robotic surgical manipulators. The full disclosure of each of these patents is incorporated by reference.

The servo-mechanisms, their supporting/positioning apparatus, the surgical instruments and endoscope/camera of a telesurgical system are typically mounted or portably positioned in the immediate vicinity of the operating table, and are referred to herein collectively as the "patient-side" portion of the telesurgical system.

Generally, a linkage mechanism is used to position and align each surgical servo-manipulator or endoscope probe with the respective incision and cannula in the patient's body. The linkage mechanism facilitates the alignment of a surgical manipulator with a desired surgical access point. Such devices will generally be referred to herein as "setup arms", it being understood that a number of quite different mechanisms may be used for this purpose. The above referenced pending PCT/US99/17522, published on Feb. 17, 2000 as WO00/07503, describes a number of aspects and examples of manipulator positioning or setup arms, and the full disclosure of this publication is incorporated by reference.

The setup arms must be supported in proximity to the surgical patient. The portion of the robotic system supported in proximity to the surgical patient may have a weight of several hundred pounds. It is desirable to support the setup arms in a manner that minimizes the relative motion between support for the setup arms and the surgical patient because the positioning of the surgical end effectors may be relative to the ground reference provided by the support for the setup arms. The mechanical path from the patient to the support for the setup arms should be stiff so that a force between the support and the patient causes a minimal displacement of the system. Various devices have been used to provide a stiff support for the setup arms.

In the system disclosed in U.S. Pat. No. 6,837,883 a patient side cart as shown in FIG. 4 supports the setup arms and the robotic surgical manipulators. While the patient side cart provides a stable support for the setup arms, it places a bulky device in the work space used by the surgical assistants and provides a tenuous connection between the setup arms and the surgical patient.

In the system disclosed in U.S. Pat. No. 6,933,695 the setup arms and the robotic surgical manipulators are supported by ceiling and floor mounted structures. While this removes a substantial amount of the support device from the work space used by the surgical assistants, it lengthens the connection between the support for the setup arms and the support for the surgical patient. This decreases the stiffness of the system and the stability of the position of the support device relative to the surgical patient.

In the system disclosed in U.S. Pat. No. 7,083,571 the setup arms and the robotic surgical manipulators are supported by the operating table using equipment rails provided along the sides of the table top. This reduces the amount of structure in the work space used by the surgical assistants and shortens the connection between the support for the setup arms and the support for the surgical patient. However, the equipment rail provided on the side of an operating table does not provide a stiff support for the relatively heavy setup arms and robotic surgical manipulators.

It would be desirable to provide a support for the setup arms and the robotic surgical manipulators of a robotic surgical system that does not unduly add to the amount of structure in the work space used by the surgical assistants and provides a rigid base of support that minimizes movement relative to the surgical patient to create a system with high stiffness.

SUMMARY

A robotic surgery system for supporting a patient and a robotic surgical manipulator. The robotic surgery system includes a base, a pillar coupled to the base at a first end and extending vertically upwardly to an opposing second end, and an attachment structure coupled to the second end of the pillar. A patient table is coupled to the attachment structure. A robot support arm has a first end coupled to the attachment structure. The robot support arm extends vertically upwardly from the first end to a second end. The robot support arm may further extend horizontally over the patient table to support a robotic surgical manipulator that will extend generally downward from the robot support arm toward a patient supported by the patient table to place an end effector of the robotic surgical manipulator adjacent a desired surgical site on the patient.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Robotic surgical systems have generally been viewed as an addition to a traditional surgical theatre. Systems intended to be added to conventional surgical suites generally make trade-offs in patient access and stiffness to accommodate the equipment found in a standard operating room. In particular, accommodating the standard operating table is a challenge for a robotic surgical system.

Embodiments of the present invention provide an integrated robotic surgery system for supporting a patient and a robotic surgical manipulator. Addressing the issues of patient support and robot support with a single system may provide advantages that are difficult to obtain with retrofit type solutions.

Figure 1:
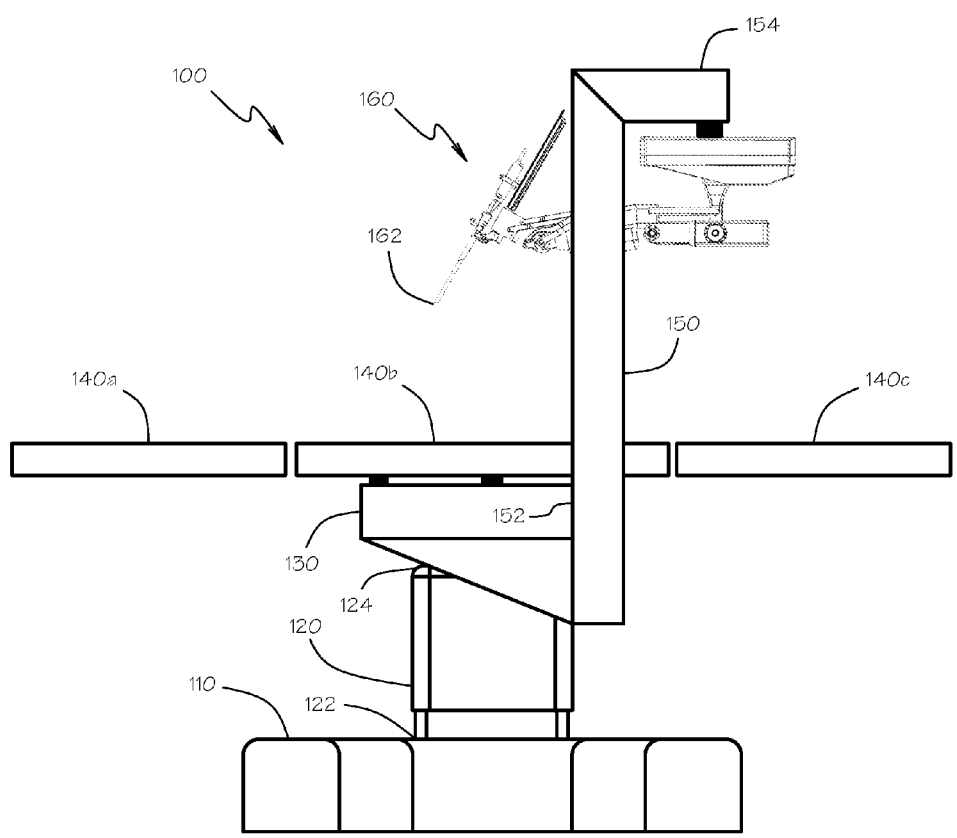
FIG. 1 is a side elevation of a robotic surgery system that embodies the invention.

FIG. 1 shows a robotic surgery system 100 that is supported by a base 110. A pillar 120 is coupled to the base 110 at a first end 122 and extends vertically upward to an opposing second end 124. An attachment structure 130 is coupled to the second end 124 of the pillar 120.

A patient table 140 is coupled to the attachment structure 130. As shown, the patient table may be an articulated structure with sections 140a, 140b, 140c that can be moved relative to one another to position the patient advantageously for surgery. Preferably the patient will be supported by the section 140b of an articulated table that is most directly coupled to the attachment structure 130.

A robot support arm 150 is coupled to the attachment structure 130 at a first end 152. The robot support arm 150 extends upward and then over the patient table 140 to a second end 154. A robotic surgical manipulator 160 may be supported adjacent the second end 154 of the robot support arm 150 and extend generally downward from the robot support arm toward a patient supported by the patient table 140 to place an end effector 162 of the robotic surgical manipulator adjacent a desired surgical site on the patient.

Advantageously the attachment structure 130 provides a substantial base that supports both the patient table 140 and the robot support arm 150. The attachment structure 130 provides a stiff coupling member between the patient support and the robot support in the robotic surgery system 100. The pillar 120 may be of a telescoping construction that can raise and lower the attachment structure 130 with respect to the base 110. The height of the attachment structure 130 with respect to the base 110 does not change the relationship between the robot support arm 150 and the patient table 140 because the attachment structure provides a common base for both.

It will be appreciated that the patient and the robotic surgical manipulators are both substantial subsystems to be supported and may be somewhat equal in weight. It will be further appreciated that the relative positions of the two subsystems are dictated by the location of the surgical site. This may require supporting one or both of the subsystems as a cantilevered load. It will be recognized that this can result in very substantial forces being imposed on the attachment structure 130, forces that are not readily borne by conventional operating room equipment.

In some embodiments of the invention the patient table 140 may be slidingly coupled to the attachment structure 130 to allow different portions of the patient to be adjacent to the end effector 162 of the robotic surgical manipulator. It will be appreciated that this may require supporting the patient substantially offset from the pillar 120 and require the base 110 to be sized and weighted to stably support such offset loads. For example, the patient may be supported largely to one side of the pillar 120 to perform head surgery.

Figure 2:
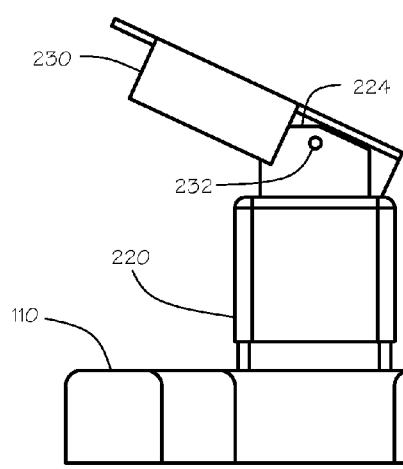
FIG. 2 is a side elevation of a portion of another robotic surgery system that embodies the invention.
Figure 3:
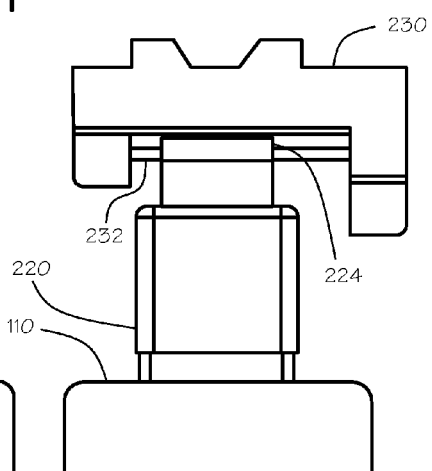
FIG. 3 is a right end view of the portion of the robotic surgery system shown in FIG. 2.

FIGS. 2 and 3 show a robotic surgery system in which the attachment structure 230 is coupled to the second end 224 of the pillar 220 with a pivotal connection 232 that allows the attachment structure to be placed at an angle to the vertical axis of the pillar. This may allow the attached patient table (not shown) to be inclined which may be desirable for certain surgeries to position internal organs by gravity effects.

Figure 4:
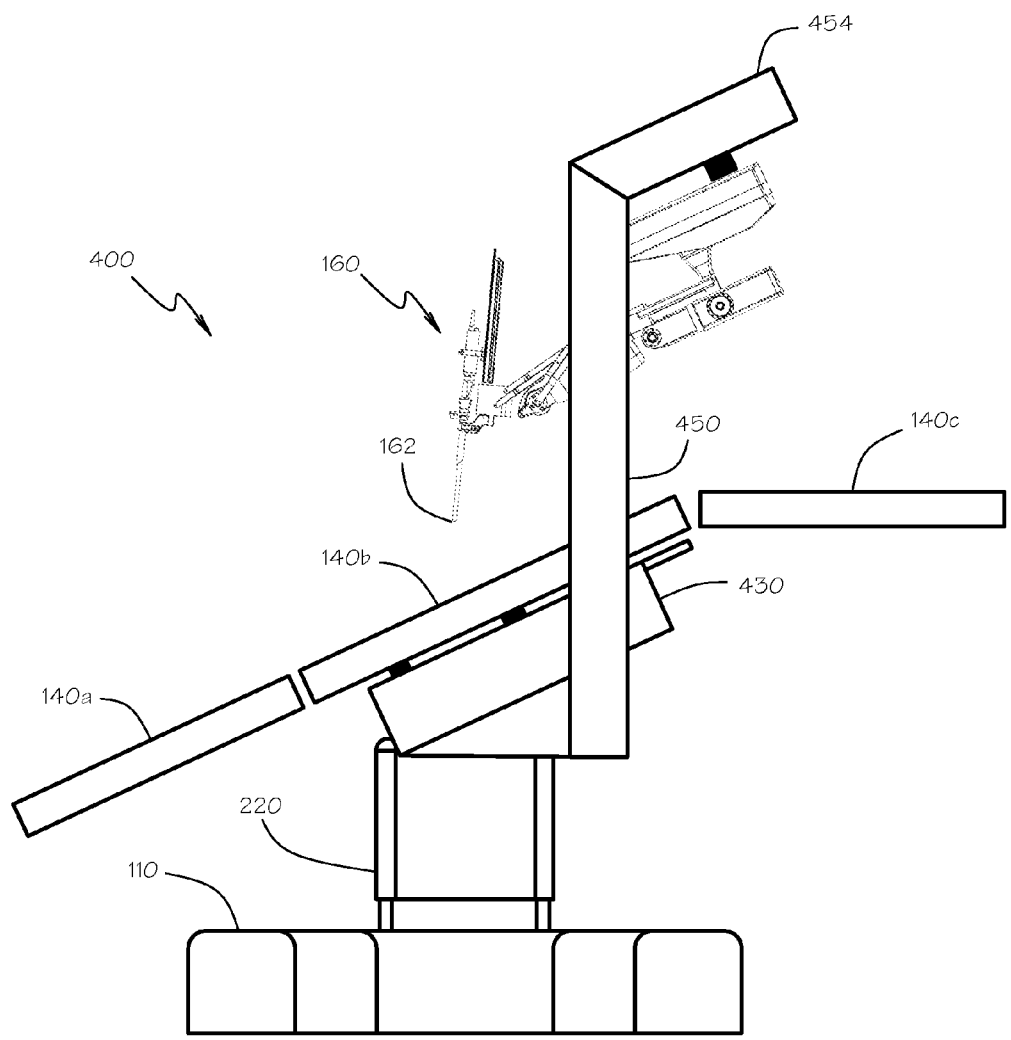
FIG. 4 is a side elevation of a portion of another robotic surgery system that embodies the invention.

FIG. 4 shows another robotic surgery system in which the attachment structure 430 is coupled to the pillar 220 with a pivotal connection that allows the attachment structure to be placed at an angle to the vertical axis of the pillar. In this embodiment the first end 452 of the robot support arm 450 is coupled to the attachment structure 430 such that the portion of the robot support arm extending upward is not perpendicular to an upper surface 432 of the attachment structure. The angle of attachment of the robot support arm 450 may be chosen to be equal and opposite to a frequently used angle of inclination of the attachment structure 430 and the attached patient table 140b. This allows the upright portion of the robot support arm 450 to be substantially vertical during many surgeries, allowing the patient-side surgeons and surgical room staff greater access to the patient and the robotic surgical equipment.

In this embodiment the second end 454 of the robot support arm 450 may be joined to the upright portion at other than a right angle so the second end 454, which supports the robotic surgical manipulator 160, is substantially parallel to the upper surface 432 of the attachment structure 430. This allows the robotic surgical manipulator 160 to be supported in a substantially horizontal position when the attachment structure 430 and the attached patient table 140b are horizontal for patient loading and initial setup of the robotic surgical manipulator.

Figure 5:
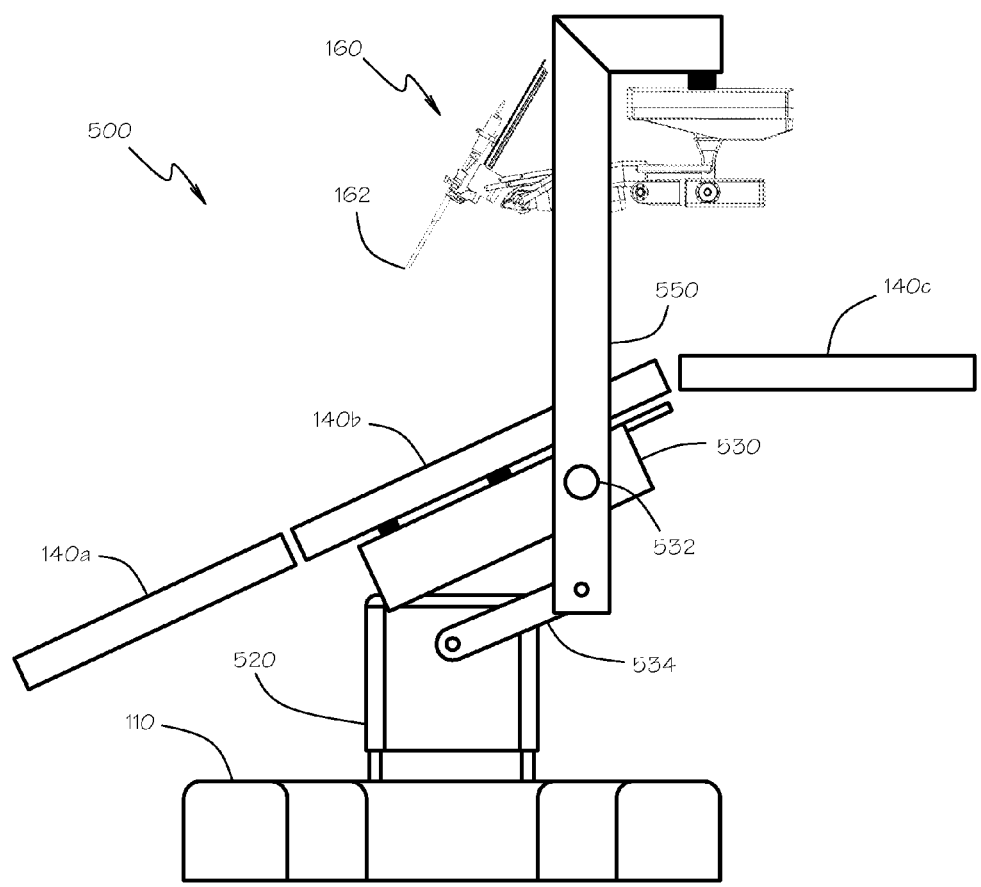
FIG. 5 is a side elevation of a portion of another robotic surgery system that embodies the invention.

FIG. 5 shows another robotic surgery system in which the attachment structure 530 is coupled to the pillar 220 with a pivotal connection that allows the attachment structure to be placed at an angle to the vertical axis of the pillar. In this embodiment the first end 552 of the robot support arm 550 is pivotally coupled 532 to the attachment structure 530. A mechanism, such as a link 534 coupled between the pillar 520 and the first end 552 of the robot support arm 550, may operate to keep the portion of the robot support arm extending upward substantially vertical as the attachment structure 530 is inclined.

Figure 6:
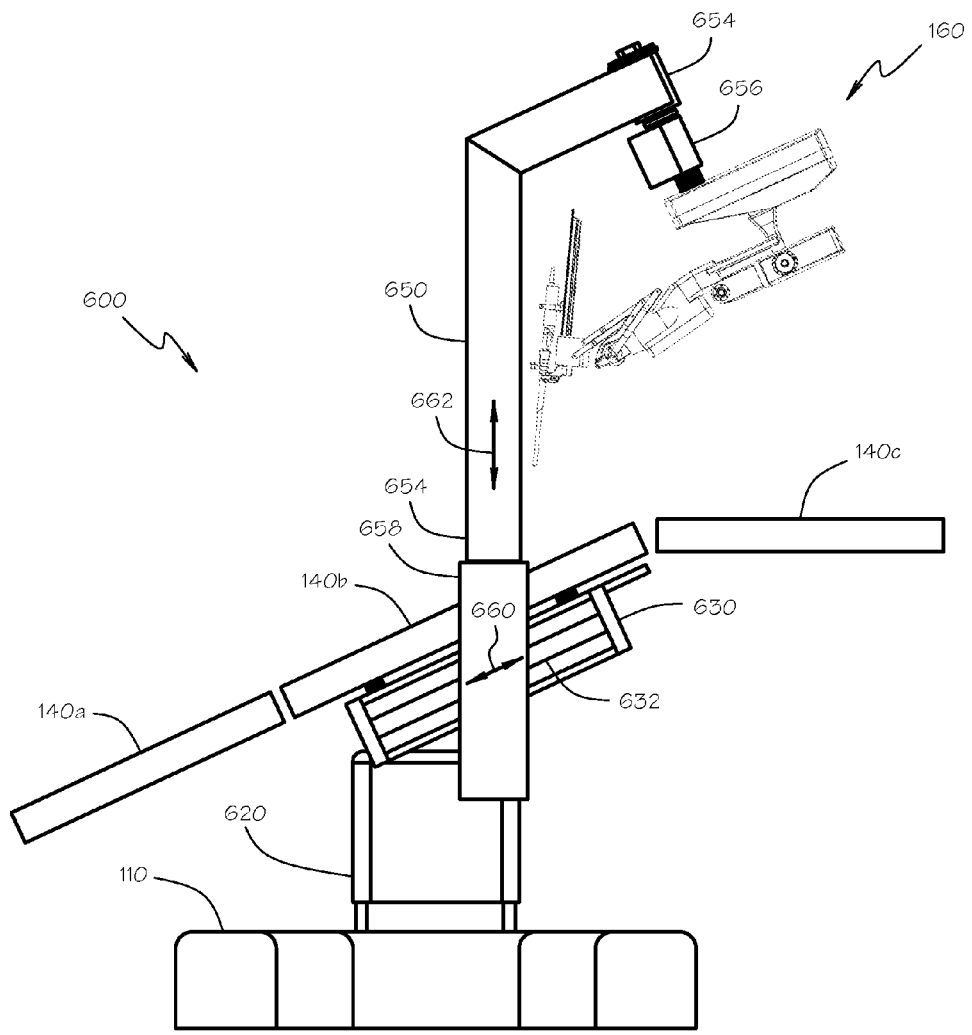
FIG. 6 is a side elevation of a portion of another robotic surgery system that embodies the invention.

FIG. 6 shows another robotic surgery system in which the first end 654 of the robot support arm 650 is coupled to the attachment structure with a sliding connection 632 that allows the robot support arm to be moved along an axis of the attachment structure as suggested by the double headed arrow 660.

The first end 654 of the robot support arm 650 may be coupled to the attachment structure with a sliding connection 658 that allows a length of the portion of the robot support arm extending upward to be adjusted as suggested by the double headed arrow 662. The sliding connection 658 may be a telescoping structure.

Figure 7:
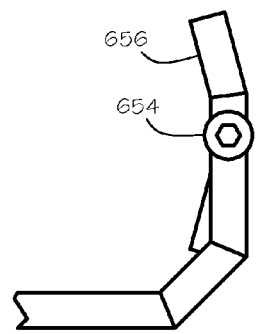
FIG. 7 is an oblique top view of a portion of the robotic surgery system shown in FIG. 6.

The robotic surgical manipulator 160 may be supported adjacent the second end 654 of the robot support arm 650 by a robot support bar 656 that is pivotally coupled to the robot support arm adjacent the second end. FIG. 7 shows an oblique view of the second end 654 of the robot support arm 650 looking along the pivot axis of the robot support bar 656. The robot support bar may support more than one robotic surgical manipulator and the bar may have a curved form to allow the end effectors 162 of several manipulators to converge on a surgical site. The pivoting of the robot support bar 656 may allow the supported robotic surgical manipulators 160 to be rotated away from the patient table 140 during patient loading onto the surgical table. In addition, the pivoting support bar may also allow the robot to be fitted with sterile covers and sterile instrumentation prior to the patient being loaded onto the table, and to maintain this sterility during pre-operative room activities, as the robot can be moved into a position where it at lower risk of being contacted by non-sterile persons or objects.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A robotic surgery system for supporting a patient and a robotic surgical manipulator, the robotic surgery system comprising:

a base sized and weighted to stably support the patient and the robotic surgical manipulator;

a pillar coupled to the base at a first end and extending vertically upward to an opposing second end;

an attachment structure coupled to the second end of the pillar;

a patient table coupled to the attachment structure; and a robot support arm having a first end coupled to the attachment structure, the robot support arm extending upwardly from the first end to a second end.

2. The robotic surgery system of claim 1 wherein the robot support arm further extends horizontally from the second end over the patient table to support the robotic surgical manipulator that will extend generally downward from the robot support arm toward the patient supported by the patient table to place an end effector of the robotic surgical manipulator adjacent a desired surgical site on the patient.

3. The robotic surgery system of claim 1 wherein the attachment structure is coupled to the second end of the pillar with a pivotal connection that allows the attachment structure to be placed at an angle to the vertical axis of the pillar.

4. The robotic surgery system of claim 1 wherein the first end of the robot support arm is coupled to the attachment structure such that the portion of the robot support arm extending upwardly is not perpendicular to an upper surface of the attachment structure.

5. The robotic surgery system of claim 1 wherein the first end of the robot support arm is coupled to the attachment structure with a sliding connection that allows a length of the portion of the robot support arm extending upwardly to be adjusted.

6. A robotic surgery system for supporting a patient and a robotic surgical manipulator, the robotic surgery system comprising:

a base;

a pillar coupled to the base at a first end and extending vertically upwardly from the first end to an opposing second end;

an attachment structure coupled to the second end of the pillar;

means for supporting a patient coupled to the attachment structure; and means for supporting a robotic surgical manipulator coupled to the attachment structure.

7. The robotic surgery system of claim 6 wherein the means for supporting the robotic surgical manipulator extends upwardly from a first end coupled to the attachment structure to a second end coupled to the robotic surgical manipulator.

8. The robotic surgery system of claim 7 wherein the means for supporting the robotic surgical manipulator further extends horizontally from the second end over the means for supporting the patient to the robotic surgical manipulator that will extend generally downward from the means for supporting the robotic surgical manipulator toward the means for supporting the patient to place an end effector of the robotic surgical manipulator adjacent a desired surgical site on the patient.

9. The robotic surgery system of claim 6 wherein the attachment structure is coupled to the second end of the pillar with a pivotal connection that allows the attachment structure to be placed at an angle to the vertical axis of the pillar.

10. The robotic surgery system of claim 6 wherein the means for supporting the robotic surgical manipulator is coupled to the attachment structure such that a portion of the means for supporting the robotic surgical manipulator extends upwardly from an upper surface of the attachment structure and is not perpendicular to the upper surface.

11. The robotic surgery system of claim 6 wherein the means for supporting the robotic surgical manipulator is coupled to the attachment structure with a sliding means for raising the means for supporting the robotic surgical manipulator relative to the means for supporting the patient.

12. A method for supporting a patient and a robotic surgical manipulator in a robotic surgery system, the method comprising:

coupling a first end of a pillar to a base such that the pillar extends vertically upwardly to an opposing second end;

coupling an attachment structure to the second end of the pillar;

coupling a patient table to the attachment structure; and coupling a first end of a robot support arm to the attachment structure, the robot support arm extending upwardly from the first end to a second end.

13. The method of claim 12 further comprising coupling the robotic surgical manipulator to the second end of the robot support arm.

14. The method of claim 12 wherein the robot support arm further extends horizontally from the second end over the patient table, and the method comprises coupling the robotic surgical manipulator to the horizontal extension of the second end such that the robotic surgical manipulator will extend generally downward from the robot support arm toward a patient supported by the patient table to place an end effector of the robotic surgical manipulator adjacent a desired surgical site on the patient.

15. The method of claim 12 wherein the attachment structure is coupled to the second end of the pillar with a pivotal connection that allows the attachment structure to be placed at an angle to the vertical axis of the pillar.

16. The method of claim 12 wherein the first end of the robot support arm is coupled to the attachment structure such that the portion of the robot support arm extending upwardly is not perpendicular to an upper surface of the attachment structure.

17. The method of claim 12 wherein the first end of the robot support arm is coupled to the attachment structure with a sliding connection that allows a length of the portion of the robot support arm extending upwardly to be adjusted.

18. The method of claim 12 wherein the first end of the robot support arm is coupled to the attachment structure with a sliding connection that allows the robot support arm to be moved along an axis of the attachment structure parallel to a length of the patient table.

19. The method of claim 12 further comprising pivotally coupling a robot support bar to the robot support arm adjacent the second end, the robotic surgical manipulator being coupled to the robot support bar, and coupling a second robotic surgical manipulator to the robot support bar.

* * * * *